United States Patent [19]

Osawa et al.

[11] Patent Number: 5,512,640
[45] Date of Patent: Apr. 30, 1996

[54] METHOD OF PRODUCING EPOXY-MODIFIED SILICONES USING ALIPHATIC ALCOHOL GELATION INHIBITORS

[75] Inventors: Yoshihito Osawa; Hiroshi Ohashi, both of Gunma, Japan

[73] Assignee: Shin-Etsu Chemical Co., Ltd., Tokyo, Japan

[21] Appl. No.: 337,001

[22] Filed: Nov. 7, 1994

[30] Foreign Application Priority Data

Nov. 8, 1993 [JP] Japan ................................ 5-303524

[51] Int. Cl.$^6$ ................................................ C08G 77/06
[52] U.S. Cl. ..................... 525/476; 525/479; 528/15; 549/214; 549/215
[58] Field of Search ........................ 525/476, 479; 528/15; 549/215, 214

[56] References Cited

U.S. PATENT DOCUMENTS

| | | | |
|---|---|---|---|
| 3,220,972 | 11/1965 | Lamoreaux | 528/15 |
| 4,028,384 | 6/1977 | Vahlensieck et al. | 549/215 |
| 4,966,981 | 10/1990 | Takai et al. | 549/215 |
| 5,128,431 | 7/1992 | Riding et al. | 528/15 |
| 5,260,399 | 11/1993 | Crivello et al. | 528/15 |

OTHER PUBLICATIONS

Chemical Abstracts 77:127297: "Synthesis of Epoxy–Novolak Resins in an Isopropyl Alcohol Medium".

*Primary Examiner*—Frederick Krass
*Attorney, Agent, or Firm*—Millen, White, Zelano, & Branigan

[57] ABSTRACT

Disclosed is a method of producing an epoxy-modified silicone, which comprises causing a reaction between (A) 100 parts of an ethylenic unsaturated group-containing epoxide and (B) from 50 to 40,000 parts of an organohydrogenpolysiloxane and/or an organohydrogensilane in the presence of (C) from 0.00001 to 0.5 part by weight, on a platinum basis, of a platinum compound as catalyst and (D) from 0.1 to 1,000 parts by weight of an aliphatic alcohol containing from 1 to 10 carbon atoms.

13 Claims, No Drawings

METHOD OF PRODUCING EPOXY-MODIFIED SILICONES USING ALIPHATIC ALCOHOL GELATION INHIBITORS

FIELD OF THE INVENTION

The present invention relates to a method of producing epoxy-modified silicones and, more particularly, to a method of producing highly pure epoxy-modified silicones wherein the gelation due to the ring-opening polymerization of epoxides can be inhibited from occurring and thereby the production efficiency can be raised.

BACKGROUND OF THE INVENTION

Hitherto, there have been known various methods for the production of organosilicones containing epoxy groups. Representatives thereof are the method of causing an olefinic group-containing siloxane to undergo a peroxidation reaction (e.g., peroxidizing vinylsiloxane with a 40% peracetic acid solution), the method of epoxidizing the siloxanes which have in advance undergone a Grignard reaction, e.g., those having the group of formula $\equiv$SiCH$_2$MgBr, through an alkali treatment in the presence of epichlorohydrin, the method of reacting chlorosilane or acetoxysilane with glycidol to produce glycidyl silicone ether (U.S. Pat. No. 2,730,532), and so forth.

However, those methods all are disadvantageous in that they are low in yield, require troublesome operations, and cannot secure consistent production.

For an industrial purpose, on the other hand, the monomers, oligomers and polymers of epoxysilicones are generally produced by the addition reaction (hydrosilylation reaction) between olefin epoxides and Si—H containing siloxanes or silanes in the presence of platinum catalyst or a catalyst for hydrosilylation use which contains platinum as a main component (Japanese Tokko Sho 43-25926, and Japanese Tokkai Sho 56-38350 and Hei 3-128975, wherein the term "Tokko" as used herein means an "examined patent publication" and the term "Tokkai" as used herein means an "unexamined published patent application").

However, the platinum catalysts are known to function not only as catalyst for the addition reaction between an olefin and Si—H but also as catalyst for the ring-opening polymerization of epoxides in the presence of Si—H.

More specifically, Japanese Tokkai Hei 3-152128 discloses the method of promoting the ring-opening reaction of epoxides by use of platinum catalyst or a catalyst containing platinum as a main component. In addition, that reference recites acetonitrile, methanol and 2-methyl-4-butene-3-ine as materials acting so as to inhibit epoxides from undergoing the ring-opening reaction. However, it has no description of the method for the production of epoxy-modified silicones.

At present the production of an epoxy-modified silicone is carried out adopting the method in which the batch temperature and the feeding speed of an olefin epoxide are carefully controlled during the reaction and, what is more, a small amount of mercaptan is used for deactivation of a platinum catalyst at the conclusion of the hydrosilylation reaction; or the method of causing the addition reaction between an olefin epoxide and Si—H in the presence of a rhodium catalyst (Japanese Tokkai Hei 4-352793).

However, inhibition of the gelation during the reaction is insufficient in the former method, while in the latter method the reaction rate is difficult to control and a long time is required to complete the reaction.

With respect to other methods for production of epoxy-silicones having high polymerization degrees, there are known the method of causing an alkali equilibrium reaction between an epoxy-containing siloxane and an epoxy-free siloxane in the presence of water in a saturated condition (Japanese Tokko Sho 51-33839), the method of causing an alkali equilibrium reaction between the foregoing siloxanes in the presence of an aprotic organic solvent (Japanese Tokkai Hei 3-255130), and so on.

Therein, however, only the addition reaction in the presence of a conventional platinum catalyst, which is capable of causing gelation through the ring-opening polymerization of an epoxy group, is instanced as a method applicable to the production of the epoxy-containing siloxane used as an intermediary raw material.

As a result of our intensive studies of the above-described problems, it has now been found that the gelation arising from the ring-opening polymerization of an epoxide in the addition reaction between an ethylenic unsaturated group-containing epoxide and a Si—H group-containing siloxane or silane in the presence of a platinum catalyst can be inhibited when a lower alcohol is added, thereby achieving the present invention.

SUMMARY OF THE INVENTION

Therefore, an object of the present invention is to provide a method of producing a highly pure epoxy-modified silicone in a high yield through the inhibition of the gelation arising from the ring-opening polymerization of an epoxide.

The above-described object of the present invention is attained with a method of producing an epoxy-modified silicone, which comprises causing a reaction between (A) 100 parts of an ethylenic unsaturated group-containing epoxide and (B) from 50 to 40,000 parts of an organohydrogenpolysiloxane and/or an organohydrogensilane in the presence of (c) from 0.00001 to 0.5 part by weight, on a platinum basis, of a platinum compound as catalyst and (D) from 0.1 to 1,000 parts by weight of an aliphatic alcohol containing from 1 to 10 carbon atoms.

DETAILED DESCRIPTION OF THE INVENTION

Suitable examples of an ethylenic unsaturated group in the ethylenic unsaturated group-containing epoxide as Component (A) include a vinyl group, an allyl group and the like.

An epoxide used for Component (A) can be properly chosen from known compounds.

Specific examples of such an epoxide include 4-vinylcyclohexene oxide, allyl glycidyl ether, methacryl glycidyl ether, 1-methyl-4isopropenylcyclohexene oxide, 2,6-dimethyl-2,3-epoxy-7-octene, 1,4-dimethyl-4-vinylcyclohexene oxide, vinylnorbornene monooxide, dicyclopentadiene monooxide, α-allyl-ω-glycidyloxy-polyethylene glycol, α-allyl-ω-glycidyloxy-polyethylene/polypropylene glycol, and so on. Of these epoxides, 4-vinylcyclohexene oxide and allyl glycidyl ether are preferred in particular.

With respect to the organohydrogenpolysiloxane or organohydrogensilane as Component (B), there can be instanced, as the former, straight-chain organohydrogenpolysiloxanes represented by general formula $[R_a(H)_bSiO_{1/2}]_2[R_2SiO]_m$ $[R(H)SiO]_n$ and cyclic organohydrogenpolysiloxanes represented by general formula $[R_2SiO]_p[R(H)SiO]_q$; while organohydrogensilanes of general formula $R_cSiH_{(4-c)}$ are examples of the latter.

Therein, R represents a monovalent organic group chosen from among alkyl groups such as methyl, ethyl, propyl, butyl, etc.; aryl groups such as phenyl, tolyl, etc.; or monovalent substituted hydrocarbon groups, e.g., monovalenthydrocarbon groups whose hydrogens are wholly or partly substituted with halogen atom(s), including chloromethyl, trifluoropropyl and the like, and monovalent hydrocarbon groups containing an alkoxy group such as methoxy, ethoxy, propoxy, etc., or a polyalkyleneoxy group.

When a plurality of R groups are present in the organohydrogenpoly siloxane or organohydrogensilane, they may be the same or different. However, it is desirable that 80 % or more of the less organic groups be methyl groups.

Further, a represents 2 or 3 and b represents 0 or 1, provided that a+b is 3; c represents 0, 1, 2 or 3; m represents 0 or an integer greater than 0, n represents 0 or an integer greater than 0, p represents 0 or an integer greater than 0, and q represents an integer of no less than 1, provided that the compound of the foregoing formula contains at least one Si—H moiety. Additionally, the straight-chain organohydrogenpolysiloxanes can contain a number of branched chain units.

Specifically, the compounds illustrated below are examples of such organohydrogenpolysiloxanes:

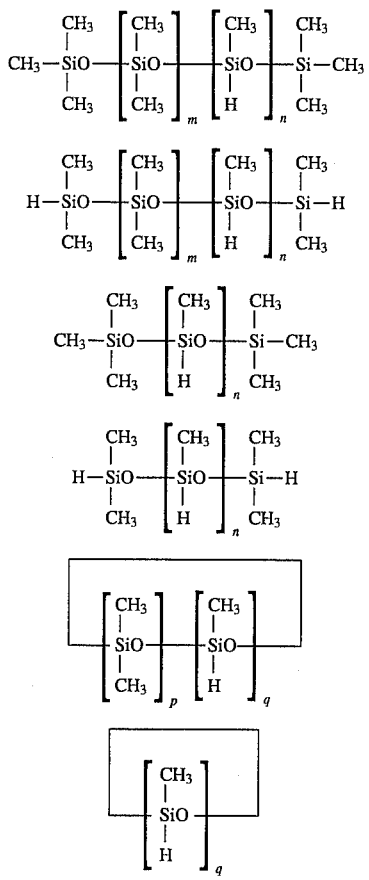

Specific examples of organohydrogensilanes include $HSi(OCH_3)_3$, $HSiCH_3(OCH_3)_2$, $HSi(OC_2H_5)_3$, $HSiCH_3(OC_2H_5)_2$ and so on.

These organohydrogenpolysiloxanes or organohydrogensilanes as component (B) are added in an amount of from 50 to 40,000 parts by weight per 100 parts by weight of an ethylenic unsaturated group-containing epoxide as Component (A). When the amount of Component (B) added is smaller than 50 parts by weight or greater than 40,000 parts by weight, the products obtained cannot serve for practical purpose.

The platinum compound catalyst as Component (C) includes platinum catalysts for addition reaction which are well known to those skilled in the art. As for the well-known platinum catalysts, chloroplatinic acid, alcohol-modified chloroplatinic acids, chloroplatinic acidvinylsiloxane complexes and the platinum compounds disclosed in U.S. Pat. Nos. 3,159,601, 3,159,662 and 3,775,452, e.g., $Pt(PPh_3)_3$, which are used for hydrosilylation reaction, are specific examples thereof.

Of these platinum compound catalysts, the alcohol-modified chloroplatinic acids and chloroplatinic acid-vinylsiloxane complexes disclosed in Japanese Tokko Sho 33-9969 are preferred over the others.

The platinum compound catalyst as Component (C) is added in an amount of from 0.00001 to 0.5 part by weight, preferably from 0.0001 to 0.05 part by weight, and particularly from 0.0005 to 0.01 part by weight, based on platinum, per 100 parts by weight of ethylenic unsaturated group-containing epoxide.

When the platinum compound is added in an amount less than 0.00001 part by weight, based on platinum, it can produce no catalytic effect; while when the amount of the platinum compound added is greater than 0.5 part by weight, based on platinum, no advantage is drawn therefrom, and so it to add the platinum compound in such an amount.

As for the aliphatic alcohol containing from 1 to 10 carbon atoms, defined as Component (D), monohydric aliphatic alcohols such as methanol, ethanol, propanol, butanol, pentanol, hexanol, octanol and decanol are examples thereof. Such an aliphatic alcohol is added in an amount of from 0.1 to 1,000 parts by weight, preferably from 1 to 100 parts by weight, per 100 parts by weight of an ethylenic unsaturated group-containing epoxide.

When the amount of Component (D) added is smaller than 0.1 part by weight, the epoxides cannot be inhibited from undergoing the ring-opening polymerization. On the other hand, when the amount thereof is increased beyond 1,000 parts by weight, no greater effect accomplished. Therefore, it is not economical to add the aliphatic alcohol in such a great amount.

In the present method for production of epoxy-modified silicones, it is desirable that the reaction system comprising Components (A), (B), (C) and (D) be kept at a temperature ranging from about 25° C. to 120° C., particularly from 50° C. to 90° C.

To the reaction system, an organic solvent such as toluene, hexane or so on can also be added with the intention of facilitating the addition and dispersion of the aforementioned components.

In accordance with the present production method, gelation due to the ring-opening polymerization of epoxides can be inhibited from occurring in the present reaction system. As a result thereof, epoxymodified silicones of high purity can be stably produced in a high yield.

The present invention will now be illustrated in more detail by reference to the following examples. However, the invention should not be construed as being limited to these examples.

EXAMPLE 1

In a one-liter reactor equipped with a stirrer were placed 152 g of 4-vinylcyclohexene oxide, 84 g of toluene, 6 g of isopropyl alcohol and 0.01 g, on a platinum basis, of chloroplatinic acid-butanol complex. After the reactor was heated up to 70°–80° C., 225 g of methylhydrogenpoly siloxane represented by the following formula (7) was added dropwise thereto, thereby running the addition reaction.

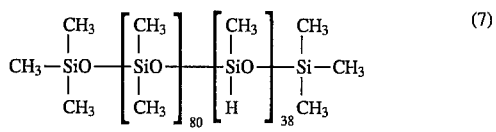

Then, the solvent was removed by stripping while the resulting mixture was being heated under reduced pressure. Thus, a transparent brown liquid having a viscosity of 5,200 cp (at 25°C.), a refractive index of 1.455 (at 25°C.), a specific gravity of 1.04 and an epoxy equivalent of 350 g/mole was obtained. From the examination by GPC (which stands for gel permeation chromatography), it was confirmed that epoxy-modified siloxane constituted 100 % of the product obtained and no high-molecular by-products due to epoxy ring-opening were observed at all.

EXAMPLE 2

In the same reactor as used in Example 1 were placed 120 g of allyl glycidyl ether, 193 g of toluene, 5 g of isopropyl alcohol and 0.001 g, on a platinum basis, of chloroplatinic acid-1,3-divinyl-1,1,3,3-tetramethyldisiloxane complex. After the reactor was heated up to 70°–80° C., 193 g of methylhydrogenpolysiloxane represented by the foregoing formula (7) was added dropwise thereto, thereby running the addition reaction.

Then, the solvent was removed by stripping while the resulting mixture was being heated under reduced pressure. Thus, a light-brown transparent liquid having a viscosity of 1,800 cp (at 25° C.), a refractive index of 1.437 (at 25° C.), a specific gravity of 1.01 and an epoxy equivalent of 340 g/mole was obtained. From the examination by GPC, it was confirmed that epoxy-modified siloxane constituted 100 % of the product obtained and no high-molecular by-products due to epoxy ring-opening were observed at all.

EXAMPLE 3

In the same reactor as used in Example 1 were placed 200 g of 4-vinylcyclohexene oxide, 200 g of toluene, 2 g of methanol and 0.005 g, on a platinum basis, of chloroplatinic acid-1,3-divinyl-1,1,3,3-tetramethyldisiloxane complex. After the reactor was heated up to 60°–70° C., 200 g of trimethoxyhydrogensilane was added dropwise thereto, thereby running the addition reaction.

Then, the solvent was removed by stripping while the resulting mixture was being heated under reduced pressure. Thus, a colorless transparent liquid having a viscosity of 5 cS (at 25° C.), a refractive index of 1.448 (at 25° C.), a specific gravity of 1.06 and an epoxy equivalent of 250 g/mole was obtained. From the examination by GPC, it was confirmed that epoxy-modified siloxane constituted 100 % of the product obtained and no high-molecular by-products due to epoxy ring-opening were observed at all.

COMPARATIVE EXAMPLE 1

The addition reaction was conducted in the same manner as in Example 1, except that isopropyl alcohol used in Example 1 was excluded. However, gelation occurred during the dropwise addition of methylhydrogensiloxane.

COMPARATIVE EXAMPLE 2

The addition reaction was conducted in the same manner as in Example 2, except that isopropyl alcohol used in Example 2 was excluded. However, gelation occurred during the dropwise addition of methylhydrogensiloxane.

COMPARATIVE EXAMPLE 3

The addition reaction was conducted in the same manner as in Example 3, except that methanol used in Example 3 was excluded. During the dropwise addition of trimethoxyhydrogensilane, an increase of viscosity was observed in the reaction solution. The product obtained was examined by GPC. As a result thereof, it was confirmed that high-molecular by-products attributable to epoxy ring-opening were present.

What is claimed is:

1. A method of producing an epoxy-modified silicone, which comprises reacting (A) 100 parts by weight of an ethylenic unsaturated group-containing epoxide with (B) from 50 to 40,000 parts by weight of an organohydrogenpolysiloxane in the presence of (C) from 0.0001 to 0.5 parts by weight, on a platinum basis, of a platinum compound as catalyst and (D) from 0.1 to 1,000 parts by weight of monohydric aliphatic alcohol having from 1 to 10 carbon atoms.

2. A method of producing an epoxy-modified silicone as claimed in claim 1, wherein the ethylenic unsaturated group-containing epoxide is selected from the group consisting of 4-vinylcyclohexene oxide, allyl glycidyl ether, methacryl glycidyl ether, 1-methyl-4-isopropenylcyclohexene oxide, 2,6-dimethyl-2,3-epoxy-7-octene, 1,4-dimethyl-4-vinylcyclohexene oxide, vinylnorbornene monooxide, dicyclopentadiene monooxide, α-allyl-ω-glycidyloxy-polyethylene glycol and α-allyl-ω-glycidyloxy-polyethylene/polypropylene glycol.

3. A method of producing an epoxy-modified silicone as claimed in claim 2, wherein the ethylenic unsaturated group-containing epoxide is 4-vinylcyclohexene oxide or allyl glycidyl ether.

4. A method of producing an epoxy-modified silicone as claimed in claim 1, wherein the organohydrogenpolysiloxane is a straight-chain organohydrogenpolysiloxane represented by the following formula $$(R_a(H)_bSiO_{1/2})_2(R_2SiO)_m(R(H)SiO)_n$$

wherein each R independently is a monovalent organic group; a is 2 or 3 and b is 0 or 1, provided that a+b is 3; m is 0 or an integer greater than 0 and n is 0 or an integer greater than 0, provided that the organohydrogenpolysiloxane contains at least one Si—H moiety.

5. A method of producing an epoxy-modified silicone as claimed in claim 1, wherein the organohydrogenpolysiloxane is a cyclic organohydrogenpolysiloxane represented by the following formula:

$$(R_2SiO)_p(R(H)SiO)_q$$

wherein each R is independently a monovalent organic group; p is 0 or an integer greater than 0; and q is an integer of no less than 1.

6. A method of producing an epoxy-modified silicone as claimed in claim 4, wherein at least 80% of organic groups present in the straight-chain organohydrogenpolysiloxane are methyl groups.

7. A method of producing an epoxy-modified silicone as claimed in claim 5, wherein at least 80% of organic groups present in the cyclic organohydrogenpolysiloxane are methyl groups.

8. A method of producing an epoxy-modified silicone as claimed in claim 1, wherein the platinum compound is selected from the group consisting of chloroplatinic acid, alcohol-modified chloroplatinic acids and chloroplatinic acid-vinylsiloxane complexes.

9. A method of producing an epoxy-modified silicone as claimed in claim 1, wherein the reaction between Component (A) and Component (B) is carried out at a temperature of 25° C. to 120° C.

10. The method of claim 1, wherein the ethylenic unsaturated group in the ethylenic unsaturated group-containing epoxide is a vinyl or allyl group.

11. The method of claim 4, wherein each R in the formula is independently methyl, ethyl, propyl, butyl, phenyl or tolyl, each optionally substituted by halogen atoms, an alkoxy group or a polyalkyleneoxy group.

12. The method of claim 5, wherein each R in the formula is independently methyl, ethyl, propyl, butyl, phenyl or tolyl, each optionally substituted by halogen atoms, an alkoxy group or a polyalkyleneoxy group.

13. The method of claim 1, wherein component (D) is used in an amount of 1 to 100 parts by weight.

* * * * *